United States Patent [19]

Porter et al.

[11] Patent Number: 5,218,137

[45] Date of Patent: Jun. 8, 1993

[54] LIGHT ACTIVATED ACYL-ENZYMES

[75] Inventors: Ned A. Porter; John D. Bruhnke, both of Durham, N.C.

[73] Assignee: Duke University, Durham, N.C.

[21] Appl. No.: 857,390

[22] Filed: Mar. 25, 1992

Related U.S. Application Data

[62] Division of Ser. No. 400,507, Aug. 20, 1989, Pat. No. 5,114,851.

[51] Int. Cl.$^5$ .................. C07C 323/00; C12N 13/00; C12N 9/76; C12N 9/70

[52] U.S. Cl. .................. 560/18; 435/213; 435/214; 435/215; 435/216; 435/217; 435/173.2; 560/34; 560/35; 560/49

[58] Field of Search ............... 435/173, 213, 214, 215, 435/216, 217; 560/18, 34, 35, 49

[56] References Cited

U.S. PATENT DOCUMENTS 4,182,897 1/1980 Fujii et al. ........................ 560/34
4,514,416 4/1985 Fujii et al. ........................ 560/49

OTHER PUBLICATIONS

Turner et al., "Photoreactivation of Irreversibly Inhibited Serine Proteinases", *J. Amer. Chem. Soc.* 1988 vol. 110 (1), 244–50.

Berezin, I. V. et al., "Detection of Light Signals by Microencapsulated cis–cinnamoyl Chymotrypsin," *Enzyme Microb. Technol.* 2, 150 (1980).

Berezin, I. V. et al., "A Flash–Induced Reaction of a Synthetic Light-Sensitive Substrate with α-chymotrypsin," *Febs Letters* 8, No. 4, 173 (1970).

Kazanskaya, N. F. et al., "Autocatalytic Enzyme System for Amplification of Light Signals," *Enzyme Microb. Technol.* 5, 209 (1983).

Martinek, K. and Berezin, I. V., "Artificial Light-Sensitive Enzymatic Systems as Chemical Amplifiers of Weak Light Signals," *Photochemistry and Photobiology* 29, 637 (1979).

McClelland, R. et al., "The Hydrolysis of Coumarin Diethyl Acetal and the Lactonization of Coumarinic Acid Ethyl Ester. The Partitioning of Tetrahedral Intermediates Generated from Independent Source," *Can. J. Chem.* 57, 2260 (1979).

Turner, A. D. et al., "Photochemical Activation of Acylated α-Thrombin," *J. Am. Chem. Soc.* 109, 1274 (1987).

Varfolomeyev, S. D. et al., "Light-Initiated Enzymic Activity Caused by Photostereoisomerization of Cis–4-Nitrocinnamoyl-α-Chymotrypsin," *Febs Letters* 15, No. 2, 118 (1971).

*Primary Examiner*—Richard L. Raymond
*Assistant Examiner*—Peter G. O'3 Sullivan
*Attorney, Agent, or Firm*—Bell, Seltzer, Park & Gibson

[57] ABSTRACT

Light activated acyl-enzymes of the formula:

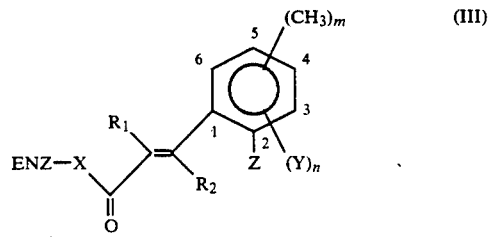

are disclosed. In the compounds of Formula (III), ENZ is an enzyme, X is O or S, Y is $-NR_3R_4$, $-OR_5$, or $-SR_5$, and Z is a nucleophile. m is 0 to 3 and n is 1 or 2. Y is substituted on the ring at either or both of the 4 and 6 position.

$R_1$ and $R_2$ are each independently H, C1 to C4 alkyl, C3 to C4 unconjugated alkenyl, or C3 to C4 unconjugated alkynyl.

$R_3$ and $R_4$ are each independently H, C1 to C4 alkyl, C3 to C4 unconjugated alkenyl, or C3 to C4 unconjugated alkynyl, except that $R_3$ and $R_4$ are not simultaneously both H. $R_5$ is C1 to C4 alkyl, C3 to C4 unconjugated alkenyl, or C3 to C4 unconjugated alkynyl.

Methods of using the acyl-enzymes and intermediates for making the acyl-enzymes are disclosed. A preferred intermediate is 2-Propenoic acid, 3-(2-hydroxy-4-diethylaminophenyl)-2-methyl-,4-(aminoiminomethyl)phenyl ester,(E)-, monohydrochloride salt, which is preferably reacted with thrombin to form an acyl-thrombin.

9 Claims, No Drawings

LIGHT ACTIVATED ACYL-ENZYMES

ACKNOWLEDGEMENT

This invention was made with the support of funds from the U.S. Government. The Government may have certain rights to this invention.

This application is a divisional of pending prior application Ser. No. 07/400,507, filed Aug. 20, 1989, now U.S. Pat. No. 5,114,851.

BACKGROUND OF THE INVENTION

Light-activatable enzymes are of interest as chemical light amplifiers and as photoactivatable therapeutic agents. As light amplifiers, the ability of a single light activated enzyme to convert thousands of molecules per minute, see generally D. Hug, 6 Photochem. Photobiol. Rev. 87 (1981), make them attractive as switches in systems such as in vitro diagnostic assays. Therapeutic uses are possible because the skin is both highly perfused by blood and accessible to light treatment. See generally J. Parrish, 77 J. Invest. Dermatology 45 (1981).

S. Varfolomeyev et al., 15 FEBS Lett. 118 (1971), describe the formation of an acyl-enzyme between α-Chymotrypsin and the p-nitrophenyl ester of p-nitro-transcinnamic acid (see Formula I, in which "ENZ" is chymotrypsin).

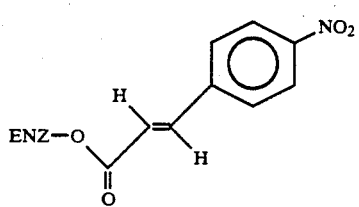

(I)

The bond between the enzyme and the acyl group is formed with the hydroxyl group of the serine at the catalytic center of the enzyme. See also I. Berezin et al., 8 FEBS Letters 173 (1970); K. Martinek et al., 29 Photochem. and Photobiol. 637 (1979); I. Berezin et al., 2 Enzyme Microb. Technol. 150 (1980); and N. Kazanskaya et al., 5 Enzyme Microb. Technol. 209 (1983). These approaches rely solely on steric effects to differentiate photoisomers. Generally the cis-cinnamoyl adduct is more stable than the trans complex, but in some cases this difference is as low as fivefold.

A. Turner et al., 109 J. Am. Chem. Soc. 1274 (1987), describe the formation of an acyl-enzyme between α-thrombin and the trans-isomer of 0-hydroxyl-α-methyl-cinnammic acid (see Formula II, in which ENZ is thrombin).

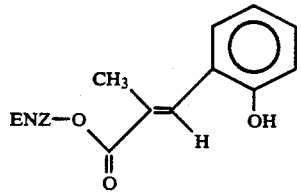

(II)

The bond between the enzyme and the acyl group is formed with the hydroxyl group of the serine at the catalytic center of the enzyme. See also A. Turner et al., 110 J. Am. Chem. Soc. 244 (1988). This compound included on the acyl group a hydroxyl group as an internal nucleophile which, on photoisomerization, leads to deacylation by attack of the internal nucleophile on the carbonyl oxygen adjacent the oxygen of the serine hydroxyl group.

Inhibition of enzyme activity in the acyl-enzyme of Formula II is temporary, and enzyme activity returns after a few hours in the dark. Furthermore, the photoactivation of these enzymes is slow and requires light intensities and wavelengths such that appreciable enzyme degradation occurs during photoactivation. Hence, there is a need for new approaches in the development of light activated acyl-enzymes. The present invention is based on our continued research in this field.

SUMMARY OF THE INVENTION

Disclosed herein are light activated acyl-enzymes of the formula:

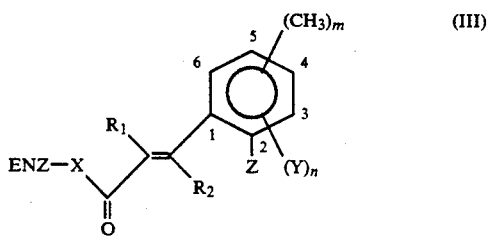

(III)

ENZ is an enzyme selected from the group consisting of serine proteinases and cysteine proteinases. X is the oxygen of the hydroxyl group in the catalytic center of ENZ when ENZ is a serine proteinase, and X is the sulfur of the sulfhydryl group in the catalytic center of ENZ when ENZ is a cysteine proteinase.

Y is selected from the group consisting of $-NR_3R_4$, $-OR_5$, and $-SR_5$. Preferably, Y is $-NR_3R_4$.

Z is a nucleophile selected from the group consisting of $-OH$, $-SH$, $-NH_2$, and $-NHR_6$ wherein $R_6$ is C1 to C4 alkyl. Preferably, Z is selected from the group consisting of $-OH$ and $-SH$.

m is 0 to 3. Preferably, m is 0 to 1, and most preferably m is 0.

n is 1 or 2, subject to the proviso that Y is substituted on the ring at the 4 position, the 6 position, or both the 4 and 6 position. Preferably, n is 1. More preferably, n is 1 and Y is substituted on the ring at the 4 position. Taken together, m and n are not greater than 5.

$R_1$ is selected from the group consisting of H, C1 to C4 alkyl, C3 to C4 unconjugated alkenyl, and C3 to C4 unconjugated alkynyl. Preferably, $R_1$ is C1 to C4 alkyl, and most preferably $R_1$ is methyl.

$R_2$ is selected from the group consisting of H, C1 to C4 alkyl, C3 to C4 unconjugated alkenyl, and C3 to C4 unconjugated alkynyl. Preferably, $R_2$ is H or C1 to C2 alkyl, and most preferably $R_2$ is H.

$R_3$ is selected from the group consisting of H, C1 to C4 alkyl, C3 to C4 unconjugated alkenyl, and C3 to C4 unconjugated alkynyl.

$R_4$ is selected from the group consisting of C1 to C4 alkyl, C3 to C4 unconjugated alkenyl, and C3 to C4 unconjugated alkynyl. Preferably, $R_3$ and $R_4$ are each independently C1 to C2 alkyl.

$R_5$ is selected from the group consisting of C1 to C4 alkyl, C3 to C4 unconjugated alkenyl, and C3 to C4 unconjugated alkynyl. Preferably, $R_5$ is C1 to C4 alkyl. Most preferably, $R_5$ is methyl.

The acyl-enzymes are used to produce an active enzyme selected from the group consisting of serine proteinases and cysteine proteinases by exposing an acyl-enzyme of Formula (III) to light at a frequency and intensity sufficient to induce trans to cis photoisomerization of the acyl-enzyme. The acyl-enzyme is then cleaved by nucleophilic attack of Z on the carbonyl oxygen adjacent X to produce the enzyme in active form.

Also disclosed herein are compounds (or "inhibitors"), useful as intermediates for making acyl-enzymes of the present invention, of the formula:

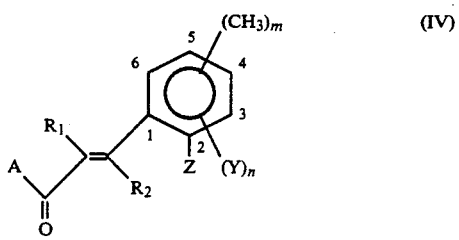

wherein A is selected from the class consisting of

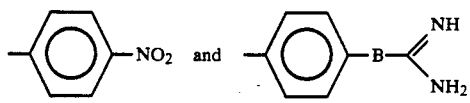

wherein B is a valence bond or —N—; and wherein Y, Z, $R_1$ and $R_2$ are the same as given in connection with the acyl-enzymes of Formula (III) above. Salts of the compounds of Formula (IV) are also disclosed.

DETAILED DESCRIPTION OF THE INVENTION

Acyl-enzymes of the present invention are made by reacting a serine proteinase or cysteine proteinase with a suitable inhibitor. The inhibitor comprises the acyl group of the acyl-enzymes of Formula (III) covalently joined to a suitable leaving group. The leaving group is selected to bind to the active site of the enzyme and form a Michealis-Menten intermediate therewith. The reaction may be carried out in aqueous solution, in accordance with the procedures used for binding the leaving group alone with the enzyme. Once the Michealis-Menten intermediate is formed, the acyl-enzyme is formed by nucleophilic attack of the hydroxyl or sulfhydryl group in the catalytic center of the enzyme on the carbonyl oxygen of the acyl group. An ester is thereby formed between the enzyme and the acyl group, with the leaving group being cleaved from the inhibitor.

Exemplary serine proteinases include, but are not limited to, Chymotrypsin, Chymotrypsin C, Metridium proteinase A, Trypsin, Thrombin, Coagulation Factor Xa, Plasmin, Enteropeptidase, Acrosin, Myxobacter α-lytic proteinase, Subtilisin, *E. coli* periplasmic proteinase, Aspergillus alkaline proteinase, Tritirachium alkaline proteinase, Arthrobacter serine proteinase, Pseudomonas serine proteinase, Thermomycolin, Thermophilic Streptomyces serine proteinase, *Candida lipolytica* serine proteinase, Alternaria serine proteinase, Tenebrio α-proteinase, Staphylococcal serine proteinase, Cathepsin G, Coagulation Factor VIIa (cattle), Coagulation Factor IXa, *Vipera russelli* proteinase, Red cell neutral endopeptidase, Cucumisin, Prolyl endopeptidase, Coagulation Factor XIa, Agkistrodon serine proteinase, *Bothrops atrox* serine proteinase, *Crotalus adamanteus* serine proteinase, Plasminogen activator (e.g., Tissue Plasminogen activator, urokinase, streptokinase), *Uca pugilator* collagenolytic proteinase, Entomophthora collagenolytic proteinase, Plasma kallikrein, Tissue kallikrein, Pancreatic elastase, Leukocyte elastase, Coagulation Factor XIIa, Chymase, Submandibular proteinase A, Complement subcomponent, Complement subcomponent, Classical-complement-pathway C3/C5 convertase, Complement Factor I, Complement Factor D, Alternative-complement-pathway C3/C5 convertase, Yeast proteinase B, Hypoderma collagenase, Achromobacter proteinase I, Leukocyte-membrane neutral endopeptidase, and Cathepsin R. See generally Enzyme Nomenclature 1984: Recommendations of the Nomenclature Committee of the International Union of Biochemistry on the Nomenclature and Classification of Enzyme-Catalysed Reactions (Academic Press, Inc. 1984)(hereinafter "Enzyme Nomenclature 1984").

Exemplary cysteine proteinases include, but are not limited to, Cathepsin B, Papain, Ficin, Bromelain, Complement component C3/C5 convertase, Baker's yeast proteinase, Lysyl bond specific proteinase, Ribosomal cathepsin, Cathepsin Bl, Papaya peptidase 1, Chymopapain, Asclepain, Clostripain, Streptococcal cysteine proteinase, gamma-Glutamyl hydrolase, Staphylococcal cysteine proteinase, Actinidin, Cathepsin L, Cathepsin H, Calpain, Prolyl endopeptidase (thiol-dependent), Clostridiopeptidase B, Streptococcal proteinase, Conjugase, Staphylococcal proteinase II, Actinidia anionic protease, Cathepsin B3, and Prolyl-(D,L)-alanin-peptidyl hydrolase. See generally Enzyme Nomenclature 1984.

The serine proteinases are preferred for practicing the present invention. More preferred are the serine proteinases of the group consisting of Trypsin, Chymotrypsin, Thrombin, Plasmin, Acrosin, Coagulation Factor $IX_a$, Coagulation Factor $X_a$, Coagulation Factor $XI_a$, Coagulation Factor $XII_a$, Plasminogen activator, Plasma kallikrein, Tissue kallikrein, Pancreatic elastase, and Leukocyte elastase.

Proteinases used for practicing the present invention may be native proteinases or derivatives of native proteinases. Derivatives of native proteinases are proteinases with amino acids added to, removed from, or changed from the amino acids found in the native proteinases. The catalytic activity of the derivative proteinase may be the same as or different from the catalytic activity of the corresponding native proteinase. All that is required is that the derivative proteinase retain activity as a proteinase and retain either a serine or hydroxyl group in the catalytic center of the enzyme.

Any group capable of forming a Michealis-Menten complex with the enzyme being used to form the acyl-enzyme, and capable of forming an ester with the acyl group to be joined to the enzyme, can be used as the leaving group. For example, imidazole derivatives are known as good substrates for α-chymotrypsin. The team at Leipzig directed by Markwardt has prepared several dozen inhibitors and assayed them with trypsin, plasmin, and thrombin. See generally F. Markwardt et al., 29 Pharmazie 333 (1974); G. Wagner et al., 28 Pharmazie 293 (1973); J. Sturzebecher et al., 35 Acta Biol.

Med. Germ. 1665 (1976); P. Walsmann, 109 Folia Haematol., Leipzig 75 (1982); V. Valenty et al., 88 Biochem. Biophys. Res. Comm. 1375 (1979); F. Markwardt et al., 28 Acta Biol. Med. Germ 19 (1972). These are compounds that lead to stable carboxylate esters of the enzyme active serine or cysteine. Other inhibitors that have been studied include compounds that react with the enzyme to generate stable sulfonate or phosphate esters. See R. Laura et al., 19 Biochemistry 4859 (1980); S. Wong and E. Shaw, 161 Ann. Biochem. and Biophys. 536 (1974). Thus, phenylmethanesulfonyl fluoride reacts to give a covalent complex with chymotrypsin and benzenesulfonyl fluoride reacts generally with trypsin, thrombin, Factor $X_a$, kallikrein, and plasmin to give serine acyl derivatives. See A. Gold and D. Fahrney, 3 Biochemistry 783 (1964). Diisopropyl fluorophosphate reacts with serine proteinases and esterases and this agent has had widespread use as an irreversible inhibitor. See P. Bracha and R. O'Brien, 9 Biochemistry 741 (1970). Indeed, a large number of compounds with the structure R—O—P(=O)(—X)—R' are inhibitors where R is an aryl or alkyl group, R' is an aryloxy, alkoxy, aryl, alkyl, or substituted amino group, and X is a leaving group (groups in brackets are bound as indicated to the last preceding nonbracketed atom).

Preferred inhibitors are given in Formula (IV). Of the preferred inhibitors, those in which p-nitrophenyl is the leaving group are preferred for use in making acyl-enzymes with digestive enzymes, such as trypsin and chymotrypsin. Those inhibitors in which either 4-amidinophenyl or 4-guanidinophenyl are the leaving groups are preferred for use in making acyl-enzymes with coagulation enzymes, such as Thrombin, Plasmin, Coagulation Factor $IX_a$, Coagulation Factor $X_a$, Coagulation Factor $XI_a$, Coagulation Factor $XII_a$, and Plasminogen activator.

The following compounds are exemplary inhibitors useful as intermediates for making acyl enzymes of the present invention. These compounds can be made by following the teaching of the Examples set forth below, taken together with known procedures.

(1) 2-propenoic acid, 3-(2-mercapto-4-diethylaminophenyl)-2-methyl-,4-(aminoiminomethyl)- phenyl ester, (E)-, monohydrochloride salt.

(2) 2-Propenoic acid, 3-(2-amino-4-diethylaminophenyl)-2-methyl-,4-(aminoiminomethyl)- phenyl ester, (E)-, monohydrochloride salt.

(3) 2-Propenoic acid, 3-(2-methylamine-4-diethylaminophenyl)-2-methyl-,4-(aminoiminomethyl)-phenyl ester, (E)-, monohydrochloride salt.

(4) 2-Propenoic acid, 3-(2-hydroxy-6-diethylaminophenyl)-2-methyl-,4-(aminoiminomethyl)- phenyl ester, (E)-, monohydrochloride salt.

(5) 2-Propenoic acid, 3-(2-hydroxy-4,6-bis(diethylamino)phenyl)-2-methyl-,4-(aminoiminomethyl)-phenyl ester, (E)-, monohydrochloride salt.

(6) 2-Propenoic acid, 3-(2-hydroxy-4-diethylamino-5-methylphenyl)-2-methyl-,4-(aminoiminomethyl)phenyl ester, (E)-, monohydrochloride salt.

(7) 2-Propenoic acid, 3-(2-hydroxy-4-diethylamino-5,6-dimethylphenyl)-2-methyl-,4-(aminoiminomethyl)-phenyl ester, (E)-, monohydrochloride salt.

(8) 2-Propenoic acid, 3-(2-hydroxy-4-diethylamino-3,5,6-trimethylphenyl)-2-methyl-,4-(aminoiminomethyl)phenyl ester, (E)-, monohydrochloride salt.

(9) 2-Propenoic acid, 3-(2-hydroxy-4-diethylaminophenyl)-2-methyl-,4-(aminoiminomethyl)- phenyl ester, (E)-, monohydrochloride salt.

(10) 2-Propenoic acid, 3-(2-hydroxy-4-diethylaminophenyl)-2-ethyl-,4-(aminoiminomethyl)phenyl ester, (E)-, monohydrochloride salt.

(11) 2-Propenoic acid, 3-(2-hydroxy-4-diethylaminophenyl)-2-propyl-,4-(aminoiminomethyl)- phenyl ester, (E)-, monohydrochloride salt.

(12) 2-Propenoic acid, 3-(2-hydroxy-4-diethylaminophenyl)-2-butyl-,4-(aminoiminomethyl)phenyl ester, (E)-, monohydrochloride salt.

(13) 2-Propenoic acid, 3-(2-hydroxy-4-diethylaminophenyl)-2-(2-propenyl)-,4-(aminoiminomethyl)phenyl ester, (E)-, monohydrochloride salt.

(14) 2-Propenoic acid, 3-(2-hydroxy-4-diethylaminophenyl)-2-(3-butenyl)-,4-(aminoiminomethyl)phenyl ester, (E)-, monohydrochloride salt.

(15) 2-propenoic acid, 3-(2-hydroxy-4-diethylaminophenyl)-2-(2-butenyl)-,4-(aminoiminomethyl)phenyl ester, (E)-, monohydrochloride salt.

(16) 2-propenoic acid, 3-(2-hydroxy-4-diethylaminophenyl)-2-(2-propenyl)-,4-(aminoiminomethyl)phenyl ester, (E)-, monohydrochloride salt.

(17) 2-Propenoic acid, 3-(2-hydroxy-4-diethylaminophenyl)-2-(3-butynyl)-,4-(aminoiminomethyl)phenyl ester, (E)-, monohydrochloride salt.

(18) 2-Propenoic acid, 3-(2-hydroxy-4-diethylaminophenyl)-2-(2-butynyl)-,4-(aminoiminomethyl)phenyl ester, (E)-, monohydrochloride salt.

(19) 2-Butenoic acid, 3-(2-hydroxy-4-diethylaminophenyl)-(2-methyl)-,4-(aminoiminomethyl)phenyl ester, (E)-, monohydrochloride salt.

(20) 2-Propenoic acid, 3-(2-hydroxy-4-diethylaminophenyl)-2-methyl-,4-(aminoiminomethyl)- phenyl ester, (E)-, monohydrochloride salt.

(21) 2-Hexenoic acid, 3-(2-hydroxy-4-diethylaminophenyl)-2-methyl-,4-(aminoiminomethyl)- phenyl ester, (E)-, monohydrochloride salt.

(22) 2-Heptenoic acid, 3-(2-hydroxy-4-diethylaminophenyl)-2-methyl-,4-(aminoiminomethyl)- phenyl ester, (E)-, monohydrochloride salt.

(23) 2,5-Hexadienoic acid, 3-(2-hydroxy-4-diethylaminophenyl)-2-methyl-,4-(aminoiminomethyl)-phenyl ester, (E)-, monohydrochloride salt.

(24) 2,6-Heptadienoic acid, 3-(2-hydroxy-4-diethylaminophenyl)-2-methyl-,4-(aminoiminomethyl)-phenyl ester, (E)-, monohydrochloride salt.

(25) 2,5-Heptadienoic acid, 3-(2-hydroxy-4-diethylaminophenyl)-2-methyl-,4-(aminoiminomethyl)-phenyl ester, (E)-, monohydrochloride salt.

(26) 2-Penten-5-ynoic acid, 3-(2-hydroxy-4-diethylaminophenyl)-2-methyl-,4-(aminoiminomethyl)-phenyl ester, (E)-, monohydrochloride salt.

(27) 2-Hepten-6-ynoic acid, 3-(2-hydroxy-4-diethylaminophenyl)-2-methyl-,4-(aminoiminomethyl)-phenyl ester, (E)-, monohydrochloride salt.

(28) 2,6-Hepten-5-ynoic acid, 3-(2-hydroxy-4-diethylaminophenyl)-2-methyl-,4-(aminoiminomethyl)-phenyl ester, (E)-, monohydrochloride salt.

(29) 2-Propenoic acid, 3-(2-hydroxy-4-ethylaminophenyl)-2-methyl-,4-(aminoiminomethyl)phenyl ester, (E)-, monohydrochloride salt.

(30) 2-Propenoic acid, 3-(2-hydroxy-4-ethylpropylaminophenyl)-2-methyl-,4-(aminoiminomethyl)-phenyl ester, (E)-, monohydrochloride salt.

(31) 2-Propenoic acid, 3-(2-hydroxy-4-butylethylaminophenyl)-2-methyl-,4-(aminoiminomethyl)phenyl ester, (E)-, monohydrochloride salt.

(32) 2-Propenoic acid, 3-(2-hydroxy-4-dimethylaminophenyl)-2-methyl-,4-(aminoiminomethyl)-phenyl ester, (E)-, monohydrochloride salt.

(33) 2-Propenoic acid, 3-(2-hydroxy-4-ethyl)(2-propenyl)aminophenyl)-2-methyl-,4-(aminoiminomethyl)phenyl ester, (E)-, monohydrochloride salt.

(34) 2-Propenoic acid, 3-(2-hydroxy-4-ethyl(3-butenyl)aminophenyl)-2-methyl-,4-(aminoiminomethyl)phenyl ester, (E)-, monohydrochloride salt.

(35) 2-Propenoic acid, 3-(2-hydroxy-4-ethyl(2-butenyl)aminophenyl)-2-methyl-,4-(aminoiminomethyl)phenyl ester, (E)-, monohydrochloride salt.

(36) 2-Propenoic acid, 3-(2-hydroxy-4-ethyl(2-propynyl)aminophenyl)-2-methyl-,4-(aminoiminomethyl)phenyl ester, (E)-, monohydrochloride salt.

(37) 2-Propenoic acid, 3-(2-hydroxy-4-ethyl(3-butynyl)aminophenyl)-2-methyl-,4-(aminoiminomethyl)phenyl ester, (E)-, monohydrochloride salt.

(38) 2-propenoic acid, 3-(2-hydroxy-4-ethyl(2-butynyl)aminophenyl)-2-methyl-,4-(aminoiminomethyl)phenyl ester, (E)-, monohydrochloride salt.

(39) 2-Propenoic acid, 3-(2-hydroxy-4-diethylaminophenyl)-2-methyl-,4-(aminoiminomethyl amino)phenyl ester, (E)-, monohydrochloride salt.

(40) 2-Propenoic acid, 3-(2-hydroxy-4-diethylaminopheny)-2-methyl-,4-(aminoiminomethyl)phenyl ester, (E)-, monoacetic acid salt.

The compounds of the present invention may be provided in the form of salts. Suitable salts include, but are not limited to, those derived from (a) inorganic acids, such as hydrochloric, hydrobromic, sulfuric and phosphoric acids, (b) organic acids such as isethionic (2-hydroxyethylsulfonic), maleic, malonic, succinic, salicylic, tartaric, lactic, citric, formic, lactobionic, pantothenic, methanesulfonic, ethanesulfonic, benzenesulfonic, p-toluenesulfonic, napathalene-2-sulfonic, and ascorbic acids, and (c) amino acids such as glycine. The acid need be a pharmaceutically acceptable acid only if the compound is intended for administration to a subject.

Acyl-enzymes of the present invention may be used by providing the acyl-enzyme in an aqueous solution, providing a substrate for the enzyme in the solution, and exposing the solution to light. The substrate undergoes a reaction catalyzed by the free enzyme after the acyl-enzyme is exposed to light. The Acyl-enzymes may be exposed to light in vivo or in vitro. When used in vitro, they may, among other things, be used as light amplifiers or light switches. For example, a diagnostic assay could be light-switched by mixing reagents, including the acyl-enzyme and a substrate for the enzyme, and then activating the enzyme by light. This provides a way to prepare numerous samples for reaction while permitting multiple reactions to proceed along a common time course by initiating the reactions simultaneously with light.

Acyl-enzymes of the present invention may be activated by exposing them to broad-spectrum light, filtered light, or monochromatic light. A 500 Watt high pressure mercury lamp, filtered or unfiltered, is one suitable light source. Preferably, wavelengths of about 300 nanometers or less are filtered from the light to which the acyl-enzymes are exposed to minimize absorption by the enzyme and light inactivation of the enzyme itself. Low intensity background light is tolerable. Most preferably, the acyl-enzymes are activated by exposing them to monochromatic light at a wavelength about equal to the absorption maximum of the acyl group.

The following examples are provided to more fully demonstrate specific aspects and embodiments of the present invention. These examples are for illustrative purposes only, and are not to be construed as limiting the invention.

EXAMPLES

The synthesis of the following compounds is disclosed in examples 1 to 8:

(A) 2-Propenoic acid, 3-(2-hydroxy-5-methoxyphenyl)-2-methyl-,4-(aminoiminomethyl)phenylester, (E)-, monohydrochloride salt (or 4-amidinophenyl-(E)-2-hydroxy-5-methoxy-α-methylcinnamate hydrochloride):

(B) 2-Propenoic acid, 3-(2-hydroxy-4-methoxyphenyl)-2-methyl-,4-(aminoiminomethyl)phenyl ester,-(E)-, monohydrochloride salt (or 4-Amidinophenyl-(E)-2-hydroxy-4-methoxy-α-methylcinnamate hydrochloride);

(C) 2-Propenoic acid, 3-(2-hydroxy-5-nitrophenyl)-2-methyl-, 4-(aminoiminomethyl)phenylester, (E)-, monohydrochloride salt (or 4-Amidinophenyl-(E)-2-hydroxy-5-nitro-α-methylcinnamate p-toluenesulphonic acid salt);

(D) 2-Propenoic acid, 3-(2-hydroxy-3,5-dimethoxyphenyl)-2-methyl-,4-(aminoiminomethyl)phenyl ester,-(E)-, monohydrochloride salt (or 4-Amidinophenyl-(E)-2-hydroxy-3,5-dimethoxy-α-methylcinnamate hydrochloride);

(E) 2-Propenoic acid, 3-(2-hydroxy-4,6-dimethoxyphenyl)-2-methyl-,4-(aminoiminomethyl)phenyl ester,-(E)-, monohydrochloride salt (or 4-Amidinophenyl-(E)-2-hydroxy-4,6-dimethoxy-α-methylcinnamate hydrochloride);

(F) 2-Propenoic acid, 3-(2-hydroxy-4-diethylaminophenyl)-2-methyl-,4-(aminoiminomethyl)phenyl ester,-(E)-, monohydrochloride salt (or 4-Amidinophenyl-(E)-2-hydroxy-4-diethylamino-α-methylcinnamate hydrochloride);

(G) 2-Propenoic acid, 3-(2-hydroxyphenyl)-2-methyl,-4-nitrophenyl ester,(E)- (or 4-Nitrophenyl-(E)-2-hydroxy-α-methylcinnamate); and (H) 2-Propenoic acid, 3-(2-hydroxy-4-diethylaminophenyl)-2-methyl-,4-nitrophenyl ester, (E)- (or 4-Nitrophenyl-(E)-2-hydroxy-4-diethylamino-α-methylcinnamate).

Compounds B, E, F, and H are inhibitors useful as intermediates for making acyl-enzymes of the present invention.

EXAMPLE 1

Synthesis of 4-amidinophenyl-(E)-2-hydroxy-5-methoxy-α-methylcinnamate hydrochloride (Compound A)

(a) Synthesis of 2-Propenoic acid, 3-(2-hydroxy-5-methoxyphenyl)-2-methyl-,ethyl ester, (E)- (or Ethyl-(E)- 2-hydroxy-5-methoxy-α-methylcinnamate). To 770.3 mg (5.06 mmol) of 5-methoxysalicylaldehyde in 20 mL of benzene at room temperature under argon was added 2.20 gm (6.08 mmol, 1.2 eq.) of (carbethoxyethylidene)- triphenylphosphorane. After one hour, the solvent was removed in vacuo, and the residue was flash column chromatographed on silica gel using 75/25 hexane/ethyl acetate as eluent to yield 1.06 gm (88%) of product; m.p. 103°–104° C. 300 MHz $^1$H-NMR (CDCL$_3$) δ 7.71 (s, 1H, β-H), 6.81 (m, 3H, aromatic-H), 5.31 (s, 1H, phenolic-H), 4.29 (q, 2H, OC$\underline{H}_2$CH$_3$, J=7.1

Hz), 3.78 (s, 3H, OCH₃), 2.04 (s, 3H, C=CCH₃), 1.38 (t, 3H, OCH₂CH₃, J=7.1 Hz). ¹³C-NMR (CDCl₃) δ 168.42, 153.07, 147.63, 133.77, 130.79, 123.28, 116.52, 115.42, 114.73, 61.08, 55.79, 14.27, 14.23. UV-lambda$_{max}$=334 nm (EtOH). TLC; 70/30 hexane/ethyl acetate, R$_f$=0.28. Anal. Calc'd for C₁₃H₁₆O₄; C, 66.09; H, 6.83. Found: C, 65.96; H, 6.88.

(b) Synthesis of 2-Propenoic acid 3-(2-hydroxy-5-methoxyphenyl-2-methyl-, (E)- (or (E)-2-Hydroxy- 5-methoxy-α-methylcinnamic acid). To a stirring solution of 318 mg (1.35 mmol) Ethyl-(E)-2-hydroxy-5-methoxy-α-methylcinnamate in 16 mL of 1:1 EtOH:-H₂O at room temperature was added 318 mg (7.95 mmol, 6 eq.) of freshly ground NaOH. The reaction was then heated at 60° C. After 45 minutes the heat was removed and the solution cooled in an ice bath. The reaction was then acidified with 10% HCl and extracted with ether. The organic phase was washed with 10% HCl, dried over MgSO₄, and concentrated in vacuo to yield 257.7 mg (92%) of product; m.p. 145°-146° C. 300 MHz¹H- NMR (CD₃OD) δ 7.81 (s, 1H, β-H), 6.82 (m, 1H, aromatic), 6.77 (m, 2H, aromatic), 4.91 (s, 2H, OH), 3.72 (s, 3H, OCH₃), 2.02 (s, 3H, C=CCH₃). ¹³C-NMR (CD₃OD) δ 172.19, 153.84, 150.95, 136.54, 129.06, 124.80, 117.13, 116.55, 116.07, 56.21, 14.42. TLC; 70/30 hexane/ethyl acetate, R$_f$=0.07. Anal. Calc'd for C₁₁H₁₂O₄; C, 63.45; H, 5.81. Found: C, 63.35; H, 5.84.

(c) Synthesis of 4-amidinophenyl-(E)-2- hydroxy-5-methoxy-α-methylcinnamate hydrochloride. To a stirring solution of 257.7 mg (1.24 mmol) (E)-2-Hydroxy-5-methoxy-α-methylcinnamic acid in 8 mL of dry pyridine at room temperature under argon was added 307 mg (1.49 mmol, 1.2 eq.) of DCC followed by 235 mg (1.36 mmol, 1.1 eq.) of p-hydroxybenzamidine hydrochloride. See G. Wagner and H. Horn, 28 Pharmazie 427 (1973); M. Partridge and W. Short, J. Chem. Soc. 390 (1947). After 48 hours the solution was filtered, concentrated in vacuo, and flash column chromatographed on 12% (w/w H₂O) deactivated silica gel using 90/10 CHCl₃/CH₃OH as eluent to yield 294 mg (65%) of product; m.p. 225°-226° C. 300 MHz¹H-NMR (CD₃OD) δ 8.09 (s, 1H, β-H), 7.89 (d, 2H, amidinophenyl-H, J=8.6 Hz), 7.46 (d, 2H, amidinophenyl-H, J=8.6 Hz), 6.92 (d, 1H, aromatic 3-position, J=2.69 Hz), 6.83 (d, 1H, aromatic 4-position, J=2.69 Hz), 6.82 (s, 1H, aromatic 6-position), 4.88 (s, exchangeable-H's), 3.77 (s, 3H, OCH₃), 2.19 (s, 3H, C=CCH₃). ¹³C-NMR (CD₃OD) δ 167.99, 157.31, 153.92, 151 35, 139.04, 130.65, 127.49, 126.85, 124.14, 124.10, 117.41, 117.27, 116.08, 56.29, 14.55. TLC; 77/23 CHCl₃/CH₃OH, R$_f$=0.25. Anal. Calc'd for C₁₈H₁₉N₂O₄Cl; C, 59.59; H, 5.28; N, 7.72. Found: C, 59.62, 59.57; H, 5.36, 5.38; N, 7.67, 7.65.

EXAMPLE 2

Synthesis of 4-Amidinophenyl-(E)-2-hydroxy-4-methoxy-α-methylcinnamate hydrochloride (Compound B)

(a) Synthesis of 2-Propenoic acid,3-(2- hydroxy-4-methoxy-phenyl)-2-methyl-,ethyl ester, (E)- (or Ethyl-(E)-2-hydroxy-4-methoxy-α-methylcinnamate. To a stirring solution of 760.8 mg (5 mmol) 4-methoxysalicylaldehyde in 20 mL benzene at room temperature under argon, was added 2.718 g (7.5 mmol, 1.2 eq.) of (carbethoxyethylidene)triphenylphosphorane. After ten minutes the solvent was removed in vacuo, and the residue was flash column chromatographed on silica gel using 80/20 hexane/ethyl acetate as eluent to yield 1.013 g (86%) of product; m.p. 104°-105° C. 300 MHz¹H-NMR (CDCl₃) δ 7.71 (s, 1H, β-H), 7.16 (d, 1H, aromatic 6-position, J=8.5 Hz), 6.50 (dd, 1H, aromatic 5-position, J=2.45, 8.5 Hz), 6.45 (d, 1H, aromatic 3-position, J=2.45 Hz), 5.74 (s, 1H, phenolic-H), 4.26 (q, 2H, OCH₂CH₃, J=7.1 Hz), 3.78 (s, 3H, CH₃O), 2.02 (s, 3H, C=CCH₃), 1.32 (t, 3H, OCH₂CH₃). ¹³C-NMR (CDCl₃) δ 169.19, 161.14, 155.44, 133.85, 130.83, 128.03, 115.53, 106.24, 101.45, 61.05, 55.31, 14.27, 14.24. TLC; 70/30 hexane/ethyl acetate, R$_f$=0.25. Anal. Calc'd for C₁₃H₁₆O₄; C, 66.09; H, 6.83. Found: C, 66.12; H, 6.86.

(b) Synthesis of 2-Propenoic acid, 3-(2- hydroxy-4-methoxyphenyl)-2-methyl-, (E)- (or (E)-2- Hydroxy-4-methoxy-α-methylcinnamic acid). To a stirring solution of 300 mg (1.27 mmol) Ethyl-(E)-2-hydroxy-4- methoxy-α-methylcinnamate in 8 mL of 1/1 EtOH/H₂O, at room temperature, was added 300 mg (7.5 mmol, 6 eq.) of freshly ground NaOH. The reaction was then heated at 60° C. for an hour. After the reaction had cooled, it was acidified with 10% HCl and extracted twice with ether. The organic phase was washed with 10% HCl, dried over MgSO₄, and concentrated in vacuo to yield 248.9 mg (94%) of product; m.p. 159°-160° C. 300 MHz¹H-NMR (CD₃OD) δ 7.86 (s, 1H, β-H), 7.26 (d, 1H, aromatic 6-position, J=8.5 Hz), 6.45 (dd, 1H, aromatic 5-position, J=2.5, 8.5 Hz), 6.40 (d, 1H, aromatic 3-position, J=2.5 Hz), 4.90 (s, broad, 2H, exchangeable-H's), 3.77 (s, 3H, CH₃O), 2.03 (s, 3H, C=CCH₃). ¹³C-NMR (CD₃OD) δ 172.77, 162.83, 158.64, 136.33, 132.09, 126.15, 117.19, 106.00, 101.99, 55.68, 14.47. TLC; 70/30 hexane/ethyl acetate, R$_f$=0.06. Anal. Calc'd for C₁₁H₁₂O₄; C, 63.45; H, 5.81. Found: C, 63.42; H, 5.82.

(c) Synthesis of 4-Amidinophenyl-(E)-2- hydroxy-4-methoxy-α-methylcinnamate hydrochloride. To a stirring solution of 230 mg (1.1 mmol) (E)-2-Hydroxy-4-methoxy-α-methylcinnamic acid in 7 mL of dry pyridine, at room temperature under argon, was added 273.5 mg (1.33 mmol, 1.2 eq.) of DCC followed by 209.7 mg (1.22 mmol, 1.1 eq.) of p-hydroxybenzamidine hydrochloride. See G. Wagner and H. Horn, 28 Pharmazie 427 (1973); M. Partridge and W. Short, J. Chem. Soc. 390 (1947). After 25 hours the reaction was filtered and concentrated in vacuo. The residue was flash column chromatographed on 12% (w/w H₂O) deactivated silica gel using 90/10 CHCl₃/CH₃OH as eluent to yield 222 mg (55.6%) of product; m.p. 198°-201° C. 300 MHZ¹H-NMR (CD₃OD) δ 8.15 (s, 1H, β-H), 7.88 (d, 2H, p-amidinophenyl-H, J=8.9 Hz), 7.43 (d, 2H, p-amidinophenyl- H, J=8.9 Hz), 7.38 (d, 1H, aromatic 6-position, J=8.5 Hz), 6.50 (dd, 1H, aromatic 5-position, J=2.4, 8.5 Hz), 6.45 (d, 1H, aromatic 3-position, J=2.4 Hz), 4.91 (s, broad, 5H, exchangeable H's), 3.79 (s, 3H, CH₃O), 2.17 (s, 3H, C=CCH₃). ¹³C-NMR (DMSO-d₆) δ 166.54, 165.07, 161.49, 158.14, 155.18, 136.60, 131.08, 129.88, 125.35, 122.79, 122.42, 114.76, 105.20, 101.05, 55.14, 14.38. TLC; 77/23 CHCl₃/CH₃OH, R$_f$=0.41. Anal. Calc'd for C₁₈H₁₉N₂O₄Cl; C, 59.59; H, 5.28; N, 7.72. Found: C, 59.57, 59.48; H, 5.29, 5.33; N, 7.68, 7.65.

EXAMPLE 3

Synthesis of 4-Amidinophenyl-(E)-2-hydroxy-5-nitro-α-methylcinnamate p-toluenesulphonic acid salt (Compound C)

(a) Synthesis of 2-Propenoic acid, 3-(2-hydroxy-5-nitrophenyl)-2-methyl-, ethyl ester, (E)- (or Ethyl-(E)-2-hydroxy-5-nitro-α-methylcinnamate). To a suspension of 1.337 g (8 mmol) 5-nitrosalicylaldehyde, in 35 mL benzene at room temperature, was added 3.479 g (9.6 mmol, 1.2 eq.) (carbethoxyethylidene)-triphenylphosphorane. After 5.25 hours the solvent was removed in vacuo, and the residue was flash column chromatographed on silica gel using 80/20 to 65/35 hexane/ethyl acetate as eluent to yield 1.629 g (81%) of product; m.p. 121°–122° C. 300 MHZ$^1$H-NMR (CDCL$_3$) δ 8.22 (d, 1H, aromatic 6-position, J=2.7 Hz), 8.18 (dd, 1H, aromatic 4-position, J=2.7, 8.8 Hz), 7.76 (s, 1H, β-H), 7.35–7.55 (broad s, 1H, phenolic-H), 7.05 (d, 1H, aromatic 3-position, J=8.8 Hz), 4.35 (q, 2H, OCH$_2$CH$_3$, J=7.1 Hz), 2.11 (s, 3H, C=CCH$_3$), 1.42 (t, 3H, OCH$_2$CH$_3$). $^{13}$C-NMR (CDCl$_3$) δ 168.63, 159.61, 141.02, 132.47, 131.85, 125.97, 125.82, 123.20, 116.05, 61.69, 14.27, 14.22. TLC; 70/30 hexane/ethyl acetate, R$_f$=0.25. UV-lambda$_{max}$=410 nm (H$_2$O). Anal. Calc'd for C$_{12}$H$_{13}$NO$_5$; C, 57.34; H, 5.22; N, 5.57. Found: C, 57.42; H, 5.23; N, 5.58.

(b) Synthesis of 2-Propenoic acid, 3-(2-hydroxy-5-nitrophenyl)-2-methyl-, (E)- (or (E)- 2-Hydroxy-5-nitro-α-methylcinnamic acid). To a stirring solution of 242 mg (0.96 mmol) Ethyl-(E)-2-hydroxy-5-nitro-α-methylcinnamate, in 10 mL of 1/1 EtOH/H$_2$O at room temperature, was added 240 mg (4.28 mmol, 4.5 eq.) of freshly ground KOH. The reaction was heated at 60° C. for 1.5 hours. The reaction was then cooled, acidified with 3% HCl, and extracted twice with ether. The organic phase was washed with 3% HCl, dried over MgSO$_4$, and concentrated in vacuo, to yield 210.3 mg (98%) of product; m.p. 235°–237° C. with decomp. 300 MHz$^1$H-NMR (CD$_3$OD) δ 8.20 (d, 1H, aromatic 6-position, J=2.7 Hz), 8.12 (dd, 1H, aromatic 4-position, J=2.7, 9.0 Hz), 7.76 (s, 1H, β-H), 6.96 (d, 1H, aromatic 3-position, J=9.0 Hz), 4.91 (s, br, 2H, exchangeable-H's), 2.06 (s, 3H, C=CCH$_3$). $^{13}$C-NMR (DMSO-d$_6$) δ 169.01, 162.07, 139.31, 131.56, 130.29, 125.95, 125.71, 123.12, 115.82, 14.05. TLC; 60/40 hexane/ethyl acetate, R$_f$=0.13. Anal. Calc'd for C$_{10}$H$_9$NO$_5$; C, 53.82; H, 4.06; N, 6.28. Found: C, 53.65; H, 4.13; N, 6.21.

(c) Synthesis of 4-Amidinophenyl-(E)-2- hydroxy-5-nitro-α-methylcinnamate p-toluenesulphonic acid salt. To a stirring solution of 146.6 mg (0.657 mmol) (E)-2-Hydroxy-5-nitro-α-methylcinnamic acid, in 3.5 mL dry pyridine at room temperature under argon, was added 165.1 mg (0.8 mmol, 1.2 eq.) of DCC followed by 258 mg (2.1 mmol, 3.2 eq.) of p-hydroxybenzamidine hydrochloride. See G. Wagner and H. Horn, 28 Pharmazie 427 (1973); M. Partridge and W. Short, J. Chem. Soc. 390 (1947). After 19.75 hours the solution was filtered and concentrated to half its original volume. The solution was then poured into saturated NaHCO$_3$ solution. The solution was filtered, and the solids were washed 3 times with H$_2$O and 4 times with acetone. The solids were then suspended in 1.5 mL CH$_3$OH, and to this was added 125 mg of p-toluenesulfonic acid monohydrate. The product, 10 mg (3%), was then forced from solution upon addition of ether. 300 MHz$^1$H-NMR (CD$_3$OD) δ 9.32 (s, br, 1H, NH), 8.81 (s, br, 1H, NH), 8.29 (s, 1H, aromatic 6-position), 8.16 (d, 1H, aromatic 4-position, J=9.0 Hz), 8.03 (s, 1H, β-H), 7.89 (d, 2H, p-amidinophenyl-H, J=8.7 Hz), 7.69 (d, 2H, toluenesulphonate-H, J=8.1 Hz), 7.47 (d, 2H, p-amidinophenyl-H, J=8.7 Hz), 7.23 (d, 2H, toluenesulphonate-H, J=8.1 Hz), 7.02 (d, 1H, aromatic 3-position, J=9.0 Hz), 4.90 (s, 3H, exchangeable-H's), 2.38 (s, 3H, CH$_3$-Ph-), 2.21 (s, 3H, C=CCH$_3$). $^{13}$C-NMR (CD$_3$OD) δ 167.37, 163.23, 157.10, 141.72, 141.46, 136.44, 130.70, 130.05, 129.84, 129.77, 127.28, 127.12, 127.02, 126.96, 124.21, 124.11, 124.05, 116.61, 21.33, 14.50. Anal. Calc'd for C$_{24}$H$_{23}$N$_3$O$_8$S; C, 56.13; H, 4.51; N, 8.13. Found: C, 55.15, 55.12; H, 4.61, 4.62; N, 7.73, 7.69.

EXAMPLE 4

Synthesis of 4-Amidinophenyl-(E)-2-hydroxy-3,5-dimethoxy-α-methylcinnamate hydrochloride (Compound D)

(a) Synthesis of 2-Propenoic acid, 3-(2- hydroxy-3,5-dimethoxyphenyl)-2-methyl-,ethyl ester,(E)- (or Ethyl-(E)-2-hydroxy-3,5-dimethoxy-α-methylcinnamate). To a stirring solution of 728.7 mg (4 mmol) 3,5-dimethoxysalicylaldehyde[1,2,3] in 20 mL benzene at room temperature under argon was added 1.74 g (4.8 mmol, 1.2 eq.) of (carbethoxyethylidene)-triphenylphosphorane. After 2 hours the solvent was removed in vacuo, and the residue was flash column chromatographed on silica gel using 80/20 hexane/ethyl acetate as eluent to yield 1.03 g (96.5%) of product. 300 MHz$^1$-NMR (CDCl$_3$) δ 7.79 (s, 1H, β-H), 6.48 (d, 1H, aromatic 6-position, J=2.8 Hz), 6.40 (d, 1H, aromatic 4-position, J=2.8 Hz), 5.51 (s, 1H, phenolic-H), 4.26 (q, 2H, OCH$_2$CH$_3$, J=7.1 Hz), 3.88 (s, 3H, 5-CH$_3$O), 3.74 (s, 3H, 3-CH$_2$O), 2.04 (s, 3H, C=CCH$_3$), 1.32 (t, 3H, OCH$_2$CH$_3$, J=7.1 HZ). $^{13}$C-NMR (CDCl$_3$) δ 168.48, 152.45, 147.01, 138.24, 133.70, 129.51, 121.87, 104.70, 99.49, 60.79, 56.07, 55.77, 14.40, 14.32. TLC; 60/40 hexane/ethyl acetate, R$_f$=0.37. Anal. Calc'd for C$_{14}$H$_{18}$O$_5$; C, 63.15; H, 6.81. Found: C, 63.07; H, 6.87.

(b) Synthesis of 2-Propenoic acid, 3-(2-hydroxy-3,5-dimethoxyphenyl)-2-methyl-, (E)- (or (E)-2-Hydroxy-3,5-dimethoxy-α-methylcinnamic acid). To a stirring solution of 1 g (3.76 mmol) Ethyl-(E)-2-hydroxy-3,5-dimethoxy-α-methylcinnamate in 24 mL of 1:1 EtOH:-H$_2$O at room temperature was added 510 mg (12.8 mmol) of freshly ground NaOH. The reaction was heated at 60° C. for 1.5 hours. After cooling, the reaction was acidified with 10% HCl and extracted twice with ether. The organic phase was washed with 10% HCl, dried over MgSO$_4$, and concentrated in vacuo to yield 839.2 mg (93.7%) of product; m.p. 210° C. with decomp. 300 MHz$^1$H-NMR (DMSO-d$_6$) δ 12.3 (s, 1H, carboxylate-H), 8.51 (s, 1H, phenolic-H), 7.71 (s, 1H, β-H), 6.59 (d, 1H, aromatic 6-position, J=2.8 Hz), 6.41 (d, 1H, aromatic 4-position, J=2.8 Hz), 3.79 (s, 3H, 5-CH$_3$O), 3.70 (s, 3H, 3-CH$_3$O), 1.97 (s, 3H, C=CCH$_3$). $^{13}$C-NMR (DMSO-d$_6$) δ 169 51, 151.76, 148.38, 139.06, 134.12, 127.84, 122.69, 104.60, 100.42, 55.93, 55.46, 14.18. TLC; 50/50 hexane/ethyl acetate, R$_f$=0.24. Anal. Calc'd for C$_{12}$H$_{14}$O$_5$; C, 60.50; H, 5.92. Found: C, 60.45; H, 5.94.

(c) Synthesis of 4-Amidinophenyl-(E)-2-hydroxy-3,5-dimethoxy-α-methylcinnamate hydrochloride. To a stirring solution of 306 mg (1.28 mmol) (E)-2-Hydroxy-3,5-dimethoxy-α-methylcinnamic acid in 8 mL dry pyridine at room temperature under argon was added 318.1 mg (1.54 mmol, 1.2 eq.) of DCC followed by 243.9 mg (1.41 mmol, 1.1 eq.) p-hydroxybenzamidine hydrochloride. See G. Wagner and H. Horn, 28 Pharmazie 427 (1973); M. Partridge and W. Short, J. Chem. Soc. 390 (1947). After 24 hours, the reaction was filtered and concentrated in vacuo. The residue was flash column chromatographed on 12% (w/w H$_2$O) deactivated silica gel using 90/10 CHCl$_3$/CH$_3$OH as eluent to yield 258.4 mg (51.4%) of product. The product was force precipitated from CH$_3$OH by addition of ether; m.p. 220°–221° C. 300 MHz$^1$H-NMR (DMSO-d$_6$) δ 9.7–8.5

(two broad singlets, 5H, exchangeable-H's), 8.01 (s, 1H, β-H), 7.93 (d, 2H, amidinophenyl-H, J=8.8 Hz), 7.49 (d, 2H, amidinophenyl-H, J=8.8 Hz), 6.66 (d, 1H, aromatic 6-position, J=2.9 Hz), 6.50 (d, 1H, aromatic 4-position, J=2.9 Hz), 3.82 (s, 3H, 5-CH$_3$O), 3.72 (s, 3H, 3-CH$_3$O), 2.12 (s, 3H, C=CCH$_3$). $^{13}$C-NMR (DMSO-d$_6$) δ 166.21, 165.07, 154.99, 151.82, 148.47, 139.50, 137.15, 129.91, 125.87, 125.50, 122.74, 121.83, 104.43, 101.17, 55.97, 55.51, 14.35. TLC; 77/23 CHCl$_3$/CH$_3$OH, R$_f$=0.44. UV-lambda=208, 228, 278, 334 nm (H$_2$O). Anal. Calc'd for C$_{19}$H$_{21}$N$_2$O$_5$Cl; C, 58.09; H, 5.39; N, 7.13. Found: C, 58.03, 57.97; H, 5.42, 5.45; N, 7.11, 7.08.

EXAMPLE 5

Synthesis of 4-Amidinophenyl-(E)-2-hydroxy-4,6-dimethoxy-α-methylcinnamate hydrochloride (Compound E)

(a) Synthesis of 2-Propenoic acid, 3-(2-hydroxy-4,6-dimethoxyphenyl)-2-methyl, ethyl ester, (E)- (or Ethyl-(E)-2-hydroxy-4,6-dimethoxy-α-methylcinnamate). To a stirring solution of 728.7 mg (4 mmol) 4,6-dimethoxysalicylaldehyde in 20 mL benzene at room temperature under argon was added 1.735 g (4.79 mmol, 1.2 eq.) of (carbethoxyethylidene)-triphenylphosphorane. After 2.5 hours the solvent was removed in vacuo, and the residue was flash column chromatographed on silica gel using 85/15 to 75/25 hexane/ethyl acetate as eluent to yield 1.011 g (94.9%) of product. 300 MHz$^1$H-NMR (CDCl$_3$) δ 7.49 (s, 1H, β-H), 6.14 (d, 1H, aromatic 3-position, J=2.3 Hz), 6.08 (d, 1H, aromatic 5-position, J=2.3 Hz), 5.44 (s, 1H, phenolic-H), 4.26 (q, 2H, OCH$_2$CH$_3$, J=7.1 Hz), 3.75-3.79 (two s, 6H, 4,6-CH$_3$O), 1.84 (s, 3H, C=CCH$_3$), 1.32 (t, 3H, OCH$_2$CH$_3$). $^{13}$C-NMR δ 167.96, 161.72, 158.71, 154.23, 131.40, 131.26, 104.39, 92.99, 91.20, 60.89, 55.59, 55.33, 14.89, 14.25. TLC; 60/40 hexane/ethyl acetate, R$_f$=0.34. Anal. Calc'd for C$_{14}$H$_{18}$O$_5$; C, 63.15; H, 6.81. Found: C, 62.94; H, 6.86.

(b) Synthesis of 2-Propenoic acid, 3-(2-hydroxy-4,6-dimethoxyphenyl)-2-methyl-, (E)- (or (E)-2- Hydroxy-4,6-dimethoxy-α-methylcinnamic acid). To a stirring solution of 965 mg (3.62 mmol) Ethyl-(E)-2- hydroxy-4,6-dimethoxy-α-methylcinnamate in 24 mL of 1:1 EtOH:H$_2$O at room temperature was added 510 mg (12.8 mmol, 3.5 eq.) of freshly ground NaOH. The reaction was then heated at 60° C. for 1.5 hours. Then it was cooled, acidified with 10% HCl, and extracted twice with ether. The organic phase was washed with 10% HCl, dried over MgSO$_4$, and concentrated in vacuo to yield 754 mg (87%) of product; m.p. 141°-142° C. 300 MHz$^1$H-NMR (CD$_3$OD) δ 7.48 (s, 1H, β-H), 6.08 (d, 1H, aromatic 3-position, J=2.2 Hz), 6.06 (d, 1H, aromatic 5-position, J=2.2 Hz), 4.91 (s (br), 2H, exchangeable H's), 3.76 (two s, 6H, 4,6-CH$_3$O), 1.73 (s, 3H, C=CCH$_3$). $^{13}$C-NMR (CD$_3$OD) δ 172.34, 163.16, 160.33, 157.50, 134.39, 130.11, 106.34, 94.43, 90.97, 55.90, 55.65, 15.51. TLC; 50/50 hexane/ethyl acetate, R$_f$=0.16. Anal. Calc'd for C$_{12}$H$_{14}$O$_5$; C, 60.50; H, 5.92. Found: C, 60.58; H 5.96.

(c) Synthesis of 4-Amidinophenyl-(E)-2-hydroxy-4,6-dimethoxy-α-methylcinnamate hydrochloride. To a stirring solution of 300 mg (1.26 mmol) (E)-2-Hydroxy-4,6-dimethoxy-α-methylcinnamic acid in 8 mL of dry pyridine at room temperature under argon was added 311.8 mg (1.51 mmol, 1.2 eq.) of DCC followed by 239.1 mg (1.39 mmol, 1.1 eq.) of p-hydroxybenzamidine hydrochloride. See G. Wagner and H. Horn, 28 Pharmazie 427 (1973); M. Partridge and W. Short, J. Chem. Soc. 390 (1947). After 26 hours the solvent was removed in vacuo, and the residue was flash column chromatographed on 12% (w/w H$_2$O) deactivated silica gel using 90/10 CHCl$_3$/CH$_3$OH as eluent to yield 356.5 mg (72%) of product; m.p. 187° C. 300 MHz$^1$H-NMR (DMSO-d$_6$) δ 8.5-9.8 (broad s, 5H, exchangeable H's), 7.90 (d, 2H, p-amidinophenyl-H, J=8.7 Hz), 7.65 (s, 1H, β-H), 7.48 (d, 2H, p-amidinophenyl-H, J=8.7 Hz), 6.18 (d, 1H, aromatic 3-position, J=2.2 Hz), 6.13 (d, 1H, aromatic 5-position, J=2.2 Hz), 3.77 (s, 3H, 6-CH$_3$O), 3.72 (s, 3H, 4-CH$_3$O), 1.81 (s, 3H, C=CCH$_3$). $^{13}$C-NMR (DMSO-d$_6$) δ 166.00, 165.05, 161.71, 158.75, 156.81, 155.03, 135.52, 129.86, 126.39, 125.40, 122.76, 103.87, 93.63, 89.82, 55.47, 55.11, 15.63. TLC; 77/23 CHCl$_3$/CH$_3$OH, R$_f$=0.39. UV-lambda=214, 304 nm (H$_2$O). Anal Calc'd for C$_{19}$H$_{21}$N$_2$O$_5$Cl; C, 58.09; H, 5.39; N, 7.13. Found: C, 57.91, 57.88; H, 5.43, 5.44; N, 7.10, 7.06.

EXAMPLE 6

Synthesis of 4-Amidinophenyl-(E)-2-hydroxy-4-diethylamino c-methylcinnamate hydrochloride (Compound F)

(a) Synthesis of 2-Propenoic acid, 3-(2-hydroxy-4-diethylaminophenyl)-2-methyl-,ethyl ester, (E)- (or Ethyl-(E)-2-hydroxy-4-diethylamino-α-methylcinnamate). To a stirring solution of 2.9 gm (15 mmol) 4-diethylaminosalicylaldehyde, in 75 mL benzene at room temperature under argon, was added 7.07 gm (19.5 mmol, 1.3 eq.) (carbethoxyethylidene)-triphenylphosphorane. After four hours at room temperature, the solvent was removed in vacuo, and the residue was flash column chromatographed on silica gel using 90/10 hexane/ethyl acetate as eluent to yield 3.52 gm (85%) of product; m.p. 102° C. 300 MHz$^1$H-NMR (CDCl$_3$) δ 7.79 (s, 1H, β-H), 7.19 (d, 1H, aromatic 6-position, J=8.8 Hz), 6.23 (dd, 1H, aromatic 5-position, J=2.3, 8.8 Hz), 6.16 (d, 1H, aromatic 3-position, J=2.3 Hz), 5.8 (s, 1H, phenolic-H), 4.22 (q, 2H, O-CH$_2$, J=7.1 Hz), 3.32 (q, 4H, N-CH$_2$, J=7.0 Hz), 2.07 (s, 1H, =C—CH$_3$), 1.31 (t, 3H, OCH$_2$CH$_3$, J=7.1 Hz), 1.14 (t, 6H, NCH$_2$CH$_3$, J=7.0 Hz). $^{13}$C-NMR (CDCl$_3$) δ 169.51, 155.89, 149.57, 133.86, 131.12, 124.51, 110.18, 104.13, 98.01, 60.69, 44.34, 14.41, 14.35, 12.62. TLC; 70/30 hexane/ethyl acetate, R$_f$=0.25. UV-lambda$_{max}$=360 nm (H$_2$O). Anal. Calc'd for C$_{16}$H$_{23}$NO$_3$; C, 69.29; H, 8.36; N, 5.05. Found: C, 69.32; H, 8.36; N, 5.04.

(b) Synthesis of 2-Propenoic acid, 3-(2-hydroxy-4-diethylaminophenyl)-2-methyl-,(E)- (or (E)-2-Hydroxy-4-diethylamino-α-methylcinnamic acid). To a stirring solution of 416 mg (1.5 mmol) Ethyl-(E)-2-hydroxy-4-diethylamino-α-methylcinnamate in 4 mL ethanol at room temperature was added 4 mL of 10% NaOH solution. The reaction was heated at 65° C. for 30 minutes and then cooled in an ice bath. The reaction was carefully acidified to pH 5 with addition of 1N HCl, extracted twice with ether, washed with saturated NH$_4$Cl solution, dried over Na$_2$SO$_4$, and concentrated to yield 365 mg (98%) of the acid. This compound decomposed upon long standing and therefore was used directly. IR (KBr) 3100-3700 (OH), 2850-3050 (C—H), 1675 (C=O), 1610 (C=C). 300 MHz$^1$H-NMR (DMSO-d$_6$) δ 11.9 (s, 1H, carboxylic-H), 9.5 (s, 1H, phenolic-H), 7.64 (s, 1H, β-H), 7.22 (d, 1H, aromatic 6-position, J=9.0 Hz), 6.18 (m, 2H, aromatic 3 and 5-positions), 3.35 (q, 4H, NCH$_2$, J=7.1 Hz), 2.0 (s, 3H, C=CCH$_3$), 1.1 (t, 6H, NCH$_2$CH$_3$). $^{13}$C-NMR (CD$_3$OD) δ 171.51, 158.60, 138.98, 134.28, 133.22, 131.24, 126.93, 113.33, 110.52, 54.73, 14.41, 10.77. TLC; 70/30 hexane/ethyl acetate, $R_f=0.04$.

(c) Synthesis of 4-Amidinophenyl-(E)-2-hydroxy-4-diethylamino-α-methylcinnamate hydrochloride. To a stirring solution of 303 mg (1.36 mmol) (E)-2- Hydroxy-4-diethylamino-α-methylcinnamic acid, in 8 mL dry pyridine at room temperature under argon, was added 336.1 mg (1.63 mmol, 1.2 eq.) of DCC followed by 257.7 mg (1.49 mmol, 1.1 eq.) of p-hydroxybenzamidine hydrochloride. See G. Wagner and H. Horn, 28 Pharmazie 427 (1973); M. Partridge and W. Short, J. Chem. Soc. 390 (1947). After 43 hours the solvent was removed in vacuo, and the residue was flash column chromatographed on 12% (w/w H$_2$O) deactivated silica gel using 90/10 CHCl$_3$/CH$_3$OH as eluent to yield 258.4 mg (47%) of product; decomp. at 125° C. 300 MHz$^1$H-NMR (CD$_3$OD) δ 8.27 (s, 1H, β-H), 7.87 (d, 2H, p-amidino-phenyl-H, J=8.7 Hz), 7.43 (d, 2H, p-amidinophenyl-H, J=8.7 Hz), 7.40 (d, 1H, aromatic 6-position, J=8.8 Hz), 6.30 (dd, 1H, aromatic-5-position, J=2.5, 8.8 Hz), 6.20 (d, 1H, aromatic 3-position, J=2.5 Hz), 4.91 (s, br, 5H, exchangeable-H's), 3.39 (q, 4H, NCH$_2$CH$_3$, J=7.1 Hz), 2.22 (s, 3H, C=CCH$_3$), 1.21 (t, 6H, NCH$_2$CH$_3$). $^{13}$C-NMR (CD$_3$OD) δ 169.12, 167.89, 159.87, 157.78, 151.84, 139.19, 132.61, 130.57, 126.43, 124.20, 119.45, 111.58, 104.82, 98.47, 45.40, 14.83, 13.07. TLC; 77/23 CHCl$_3$/CH$_2$OH, $R_f=0.28$. UV-lambda$_{max}$=378 nm (H$_2$O). Anal. Calc'd for C$_{21}$H$_{26}$N$_3$O$_3$Cl; C, 62.45; H, 6.49; N, 10.40. Found: C, 62.29, 62.22; H, 6.52, 6.55; N, 10.34, 10.28.

EXAMPLE 7

Synthesis of 4-Nitrophenyl-(E)-2-hydroxy-α-methylcinnamate (Compound G)

To 113.6 mg (0.637 mmol) of trans-o-hydroxy-α-methylcinnamic acid, see Sinhababu, A. K. and Borchardt, R. T., J. Org. Chem. 48, 2356 (1983), in 5 mL of dry pyridine at room temperature under argon was added 160.6 mg (0.778 mmol, 1.2 eq.) of DCC, followed by addition of 98.5 mg (0.708 mmol, 1.1 eq.) of p-nitrophenol. The reaction was let stir under argon for approximately 26 hours. The solution was then filtered and the pyridine was removed in vacuo. The residue was flash column chromatographed on silica gel using 9:1 benzene:ethyl acetate as eluent to give an 80% yield of white powder; m.p. 166°-170° C. 300 MHz$^1$H-NMR (DMSO-d$_6$) δ 10.02 (s, 1H, phenolic-H), 8.31 (d, 2H, p-nitrophenyl 3-position, J=9.23 Hz), 8.04 (s, 1H, β-H), 7.53 (d, 2H, p-nitrophenyl 2-position, J=9.23 Hz), 7.39 (d, 1H, aromatic 6-position, J=8.25 Hz), 7.25 (dt, 1H, aromatic 4-position, J=1.52, 8.25 Hz), 6.94 (d, 1H, aromatic 3-position, J=8.25 Hz), 6.88 (t, 1H, aromatic 5-position, J=8.25 Hz), 2.15 (s, 3H, C=CCH$_3$). $^{13}$C-NMR (DMSO-d$_6$) δ 165.97, 156.27, 155.93, 144.97, 137.28, 130.80, 130.05, 125.28, 125.21, 123.36, 121.73, 118.90, 115.65, 14.26. Anal. Calc'd for C$_{16}$H$_{13}$NO$_5$; C, 64.21; H, 4.38; N, 4.68. Found: C, 63.98, 64.32; H, 4.76, 4.41; N, 4.91, 4.62.

EXAMPLE 8

Synthesis of 4-Nitrophenyl-(E)-2-Hydroxy-4-diethylamino-α-methylcinnamate (Compound H)

To a stirring solution of 860 mg (3.45 mmol) (E)-2-hydroxy-5-methoxy-α-methylcinammic acid in 7 mL dry pyridine at room temperature under argon was added 854.1 mg (4.14 mmol, 1.2 eq.) of DCC, followed by 575.8 mg (4.14 mmol, 1.2 eq.) of p-nitrophenol and a catalytic amount of dimethylaminopyridine. After approximately 26 hours at room temperature the reaction was filtered, and solvent was removed in vacuo. The residue was flash column chromatographed on silica gel using 9:1 benzene:ethyl acetate as eluent to yield 1.26 gm (99%) of product; m.p. 124°-129° C. 300 MHz$^1$H-NMR (DMSO-d$_6$) δ 9.69 (s, 1H, phenolic-H), 8.32 (d, 2H, p-nitrophenyl 3-position, J=9.0 Hz), 8.18 (s, 1H, β-H), 7.49 (d, 2H, p-nitrophenyl 2-position, J=9.0 Hz), 7.39 (d, 1H, aromatic 6-position, J=8.9 Hz), 6.22 (dd, 1H, aromatic 5-position, J=2.2, 8.9 Hz), 6.21 (d, 1H, aromatic 3-position, J=2.2 Hz), 3.38 (q, 4H, NCH2, J=7.1 Hz), 2.18 (s, 3H, C=CCH$_3$), 1.17 (t, 6H, NCH$_2$CH$_3$, J=7.1 Hz). $^{13}$C-NMR (DMSO-d$_6$) δ 166.64, 158.60, 156.46, 150.03, 144.67, 137.15, 131.28, 125.19, 123.36, 117.28, 109.51, 103.37, 97.13, 43.85, 14.52, 12.61. Anal. Calc'd for C$_{20}$H$_{22}$N$_2$O$_5$; C, 64.85; H, 5.99; N, 7.56. Found: C, 64.95; H, 6.05; N, 7.53.

EXAMPLE 9

(COMPARATIVE EXAMPLE A)

Acylation of Thrombin with 4-Amidinophenyl-(E)-2-hydroxy-4-diethylamino-α-methylcinnamate (Compound F)

The reaction of 4-Amidinophenyl-(E)-2-hydroxy-4-diethylamino-α-methylcinnamate hydrocholoride (Compound F) with thrombin to form an acyl-thrombin (hereinafter "DEA acyl-thrombin") was monitored by chromogenic assay. See A. Turner, et al., 110 J. Am. Chem. Soc. 244 (1988); B. Blomback, Theoretical Considerations of Substrate Structures Governing Enzyme Specificity, 3 (M. Scully and V. Kakkar eds 1979)(New York: Churchill Livingston). A 1- to 5- fold excess of 4-Amidinophenyl-(E)-2-hydroxy-4-diethylamino-α-methylcinnamate with thrombin (1.5 μM) in pH 7.4 Tris buffer led to complete loss of thrombin activity in less than 1 hour. Gel filtration of the resulting inactive thrombin solution on Sephadex G-25 with pH 7.4 Tris buffer solvent gave acyl enzyme eluting identically to active thrombin, but with less than 2% activity. In the dark, thrombin activity of this solution increased in a clean first-order process with a rate of 1.4·10$^{-6}$ s$^{-1}$ (half-life for activation=138 hours).

For comparison, the half-life for reactivation of an acyl thrombin formed in the same manner from 4-Amidinophenyl-(E)-2-hydroxy-α-methylcinnamate and thrombin (hereinafter "acyl-thrombin") was 3.8 hours.

The p-diethylamino group of 4-Amidinophenyl-(E)-2-hydroxy-4-diethylamino-α-methylcinnamate gives a characteristic chromophore 360 nm=lambda$_{max}$. Assuming an ε of DEA acyl-thrombin equal to that of the corresponding ethyl ester, Ethyl-(E)-2-hydroxy-4-diethylamino-α-methylcinnamate, (ε=22400), we conclude that the purified DEA acyl-thrombin has one attached acyl group. These data support the notion that 4-Amidinophenyl-(E)-2-hydroxy-α-methylcinnamate and 4-Amidinophenyl-(E)-2-hydroxy-4-diethylamino-α-methylcinnamate (Compound F) acylate the serine active site hydroxyl of thrombin to give acyl-thrombin and DEA acyl-thrombin. The p-diethylamino group of DEA acyl-thrombin presumably donates electron density by resonance and stabilizes the acyl enzyme. See R. Kogan and T. Fife, 23 Biochemistry 2983 (1984); F. Markwardt, et al., 28 Acta. Biol. Med. Germ. 19 (1972).

EXAMPLE 10

(COMPARATIVE EXAMPLE B)

Rate Constants for 4-Amidinophenyl-(()-2-hydroxy-4-diethylamino-α-methylcinnamate (Compound F)

We report here rate constants for our best inhibitor, 4-Amidinophenyl-(E)-2-hydroxy-4-diethylamino-α-methylcinnamate hydrochloride (Compound F). These data allow a description of the time course of the photoactivation process.

Preliminary to our studies of the enzyme system, we studied the photochemistry of the model compounds Ethyl-(E)-2-methoxy-4-diethylamino-α-methylcinnamate and Ethyl-(E)-2-hydroxy-4-diethylamino-α-methylcinnamate (hereinafter "DEA acyl", as this compound models DEA acyl-thrombin with ethyl in place of thrombin). Photolysis of Ethyl-(E)-2-methoxy-4-diethylamino-α-methylcinnamate with 366 nm light results in a rapid decrease in absorbance as the cis photoisomer is formed (In all photolyses reported here, except for the laser flash studies, the source lamp was a mercury 500 W high pressure lamp. The 366 nm emission was isolated by a Bausch and Lomb grating monochromator). At the photostationary state, the cis photoisomer is 60% of the mixture, and the $\epsilon$ of the cis compound is <40% of that of the trans at 360 nm. Photolysis for 5 minutes of DEA acyl in 98% ethanol/2% pH 7.4 Tris buffer gives a sharp decrease in the absorbance at 360 nm, followed by a slow increase in absorbance at 380 nm due to the dark formation of the 3-methyl-7-N,N-diethylamino-coumarin (hereafter "the coumarin"). The increase in the absorbance due to the coumarin is first order with $k_c = 7.17 \cdot 10^{-4} \, s^{-1}$. The presence of the cis isomer has been confirmed by NMR after photolysis as $<0°$ C. The rate of cyclization of cis DEA acyl is solvent dependent and increases by two orders of magnitude in 50/50 ethanol/Tris buffer (Table 1). Photolysis of trans DEA acyl in Tris buffer alone gives a clean conversion to coumarin with an isosbestic point observed at 370 nm. Thus, in Tris and using conventional spectroscopy, there is no evidence for the formation of cis DEA acyl in the conversion of the trans isomer to coumarin, but flash photolysis experiments (vide infra) indicate that the cis intermediate is formed, but is very reactive in this solvent. The yield of coumarin from DEA acyl is essentially quantitative under all of the conditions described.

Photolysis of DEA acyl-thrombin (2.0 μM in pH 7.4 Tris) with monochromatic 366 nm light for 25 seconds leads to the formation of fully active enzyme (by chromogenic assay) and 1 equivalent of coumarin, as determined by gas chromatography and fluorescence of 4 at 480 nm. No evidence for a cis acyl enzyme photoisomer is seen by conventional spectroscopy. However, flash photolysis (10 nsec) of DEA acyl or DEA acyl-thrombin in Tris buffer with 355 nm light from a Nd/Yad laser does give evidence for the cis photoisomer. For both DEA acyl and DEA acyl-thrombin, the flash results in an immediate decrease in absorbance at 380 nm, followed by a first order increase of absorbance as the coumarin forms from the cis intermediate. The important first order rate constants determined in this study are presented in Table 1.

TABLE 1

First Order Rate Constants for Enzyme Deacylation and Cyclization of Cis Photoisomers at 23° C.

| Compound | Solvent | First Order Rate Constant, $s^{*1}$ | Half-Life Half-Life |
|---|---|---|---|
| trans acyl-thrombin | Tris pH 7.4 | $5.0 \pm 0.5 \cdot 10^{-5}$ | 3.8 h[a] |
| trans DEA acyl-thrombin | Tris pH 7.4 | $1.4 \pm 0.2 \cdot 10^{-6}$ | 138. h[a] |
| cis DEA acyl | 98/2 ethanol/Tris pH 7.4 | $7.2 \pm 0.2 \cdot 10^{-4}$ | 16.1 min[b] |
| cis DEA acyl | 50/50 ethanol/Tris pH 7.4 | $9.7 \pm 1.4 \cdot 10^{-2}$ | 7.1 sec[b] |
| cis DEA acyl | 2/98 ethanol/Tris pH 7.4 | $1.7 \pm 0.5$ | 0.4 sec[b, c] |
| cis DEA acyl-thrombin | 2/98 ethanol/Tris pH 7.4 | $2.4 \pm 0.2 \cdot 10^3$ | 287 μsec[b, c] |

[a]Half-life of trans-acyl enzyme deacylation.
[b]Half-life of cyclization to give the coumarin.
[c]Flash photolysis.

The deacylation of cis DEA acyl-thrombin is $>10^9$ faster than the deacylation of trans DEA acyl-thrombin. This results from the mechanism of deacylation involved, since the internal nucleophile on the cinnamate aromatic ring cannot attack the carbonyl of the enzyme serine ester if the alkene is trans. Photoisomerization presents the nucleophile to the reactive site for deacylation and the lactonization of the cis alkene is a rapid process in the enzyme active site. See R. McClelland et al., 57 *Can. J. Chem,* 2260 (1979); S. Milstein amd L. Cohen, 67 *Proc. Natl. Acad. Sci. U.S.A.* 1143 (1970).

Comparison of the deacylation rates of DEA acyl-thrombin and DEA acyl is also of interest. Under the same conditions of solvent and temperature cis DEA acyl-thrombin lactonizes 1000 times faster than cis DEA acyl. The enzyme active site has a histidine-aspartic acid shuttle, (Creighton, T. E., *Proteins, Structures and Molecular Principles,* New York: W. H. Freeman and Company 1984, 427) to provide the requisite proton to the serine hydroxyl leaving group and to accept the proton from the phenolic nucleophile. The normal catalytic activity of the enzyme thus apparently assists in the deacylation once the internal nucleophile is presented to the active site by photoisomerization. Active site catalysis of processes such as dehydrohalogenation and lactamization of acyl serine proteases has been the subject of other important studies. See C. Kam et al., 27 *Biochemistry* 2547 (1988); A. Krantz et al., 30 *J. Med. Chem.* 589 (1987); R. Westkaemper and R. abeles, 19 Biochemistry 3256 (1983); L. Hedstrom et al., 23 Biochemistry 1753 (1984).

The foregoing examples are illustrative of the present invention, and are not to be taken as restrictive thereof. The invention is defined by the following claims, with equivalents of the claims to be included therein.

That which is claimed is:

1. A compound useful as an intermediate for making light-activatable acyl-enzymes, said compound being of the formula:

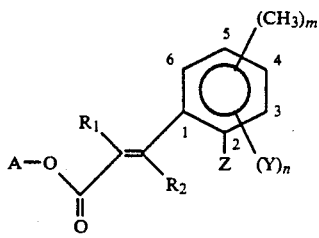

wherein A is selected from the class consisting of

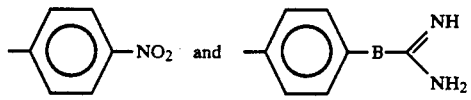

wherein

B is a valence bond or —N—;

Y is selected from the group consisting of —NR$_3$R$_4$, OR$_5$, and —SR$_5$;

Z is a nucleophile selected from the group consisting of —OH, —SH, —NH$_2$, and —NHR$_6$ wherein R$_6$ is C1 to C4 alkyl;

m is 0 to 3;

n is 1 or 2, subject to the proviso that Y is substituted on said ring at said 4 position, said 6 position, or both said 4 and 6 position;

R$_1$ is selected from the group consisting of H, C1 to C4 alkyl, C3 to C4 unconjugated alkenyl, and C3 to C4 unconjugated alkynyl;

R$_2$ is selected from the group consisting of H, C1 to C4 alkyl, C3 to C4 unconjugated alkenyl, and C3 to C4 unconjugated alkynyl;

R$_3$ is selected from the group consisting of H, C1 to C4 alkyl, C3 to C4 unconjugated alkenyl, and C3 to C4 unconjugated alkynyl;

R$_4$ is selected from the group consisting of C1 to C4 alkyl, C3 to C4 unconjugated alkenyl, and C3 to C4 unconjugated alkynyl; and R$_5$ is selected from the group consisting of C1 to C4 alkyl, C3 to C4 unconjugated alkenyl, and C3 to C4 unconjugated alkynyl;

or a salt thereof.

2. A compound according to claim 1, wherein Y is —NR$_3$R$_4$.

3. A compound according to claim 1, wherein Z is a nucleophile selected from the group consisting of —SH and —OH.

4. A compound according to claim 1, wherein m is 0 to 1.

5. A compound according to claim 1, wherein n is 1.

6. A compound according to claim 1, wherein R$_1$ is C1 to C4 alkyl.

7. A compound according to claim 1, wherein R$_2$ is H or C1 to C2 alkyl.

8. A compound according to claim 1, wherein R$_3$ and R$_4$ are each independently C1 to C2 alkyl.

9. A compound according to claim 1, wherein:

Y is —NR$_3$R$_4$;

Z is a nucleophile selected from the group consisting of —SH and —OH;

m is 0 to 1;

n is 1;

R$_1$ is C1 to C4 alkyl;

R$_2$ is H or C1 to C2 alkyl; and

R$_3$ and R$_4$ are each independently C1 to C2 alkyl.

* * * * *

UNITED STATES PATENT AND TRADEMARK OFFICE
CERTIFICATE OF CORRECTION

PATENT NO. : 5,218,137
DATED : June 8, 1993
INVENTOR(S) : Ned A. Porter and John D. Bruhnke It is certified that error appears in the above-identified patent and that said Letters Patent is hereby corrected as shown below:

Column 9, Line 48, Example 1, correct "151 35," to read -- 151.35,--.

Column 12, Line 24, Example 4, correct "3-C$\underline{H}_2$O" to read --3-C$\underline{H}_3$O--.

Column 12, Line 48, Example 4, correct "169 51" to read -- 169.51 --.

Column 14, Line 23, Example 6, correct "c-methylcinnamate" to read --α-methylcinnamate--.

Column 15, Line 13, Example 6, correct " 43 hours " to read -- 40 hours --.

Column 17, Line 5, Example 10, correct "(()-2" to read -- (E)-2 --.

Column 18, Line 13, Table 1, please move pH 7.4 under Solvent column.

Signed and Sealed this

Eighteenth Day of January, 1994

Attest:

BRUCE LEHMAN

*Attesting Officer*     *Commissioner of Patents and Trademarks*